(12) United States Patent
Kubota et al.

(10) Patent No.: US 12,333,727 B2
(45) Date of Patent: Jun. 17, 2025

(54) ENDOSCOPE APPARATUS, INFORMATION PROCESSING METHOD, AND STORAGE MEDIUM

(71) Applicant: OLYMPUS CORPORATION, Tokyo (JP)

(72) Inventors: Akihiro Kubota, Kokubunji (JP); Yamato Kanda, Hino (JP); Makoto Kitamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 416 days.

(21) Appl. No.: 17/873,243

(22) Filed: Jul. 26, 2022

(65) Prior Publication Data
US 2022/0375089 A1 Nov. 24, 2022

Related U.S. Application Data

(63) Continuation of application No. PCT/JP2020/005077, filed on Feb. 10, 2020.

(51) Int. Cl.
*G06T 7/00* (2017.01)
*A61B 1/00* (2006.01)
(Continued)

(52) U.S. Cl.
CPC .......... *G06T 7/0014* (2013.01); *A61B 1/0005* (2013.01); *A61B 1/06* (2013.01);
(Continued)

(58) Field of Classification Search
CPC .......... A61B 1/00006; A61B 1/000094; A61B 1/000095; A61B 1/0005; A61B 1/00055;
(Continued)

(56) References Cited

U.S. PATENT DOCUMENTS

| 6,857,878 B1 * | 2/2005 | Chosack | G09B 23/285 |
| | | | 434/262 |
| 2014/0081083 A1 * | 3/2014 | Morita | A61B 1/00177 |
| | | | 600/109 |

(Continued)

FOREIGN PATENT DOCUMENTS

| JP | H03153208 A | 7/1991 |
| JP | H11337842 A | 12/1999 |

(Continued)

OTHER PUBLICATIONS

International Search Report dated Apr. 21, 2020 issued in PCT/JP2020/005077.

*Primary Examiner* — Dakshesh D Parikh
(74) *Attorney, Agent, or Firm* — Scully, Scott, Murphy & Presser, P.C.

(57) ABSTRACT

An endoscope apparatus includes a processor. The processor conducts analysis whether an endoscope image has been appropriately captured or not on the basis of the endoscope image. The processor acquires correction restriction information that is at least one of a restriction regarding a size of a lumen of an image-captured portion or a restriction regarding a submucosa state of the image-captured portion. The processor generates correction information regarding correction of image-capturing conditions for allowing the endoscope image to be appropriately captured under a restriction of the correction restriction information in a case where it is analyzed that the endoscope image has not been appropriately captured, and outputs the correction information on a monitor.

25 Claims, 11 Drawing Sheets

(51) Int. Cl.
*A61B 1/06* (2006.01)
*A61B 1/12* (2006.01)
*G06T 7/55* (2017.01)
*G06T 7/73* (2017.01)

(52) U.S. Cl.
CPC ............... *A61B 1/126* (2013.01); *G06T 7/55* (2017.01); *G06T 7/74* (2017.01); *G06T 2207/10068* (2013.01); *G06T 2207/30004* (2013.01)

(58) Field of Classification Search
CPC ......... A61B 1/045; A61B 1/06; A61B 1/0655; A61B 1/126; G06T 2207/10068; G06T 2207/30004; G06T 7/0014; G06T 7/55; G06T 7/74
See application file for complete search history.

(56) References Cited

U.S. PATENT DOCUMENTS

| | | |
|---|---|---|
| 2016/0324398 A1 | 11/2016 | Sasaki |
| 2018/0084970 A1 | 3/2018 | Harada et al. |
| 2018/0242818 A1 | 8/2018 | Kubo et al. |

FOREIGN PATENT DOCUMENTS

| | | | | |
|---|---|---|---|---|
| JP | 2003250760 A | | 9/2003 | |
| JP | 2006280425 A | * | 10/2006 | ............... A61B 1/00 |
| JP | 2014113416 A | | 6/2014 | |
| JP | 2018050890 A | | 4/2018 | |
| JP | 2018139846 A | | 9/2018 | |
| JP | 2018139847 A | * | 9/2018 | ............. A61B 1/045 |
| WO | 2015111560 A1 | | 7/2015 | |
| WO | 2018159347 A1 | | 9/2018 | |

* cited by examiner

FIG. 6

| | |
|---|---|
| IMAGE QUALITY ANALYSIS | $\alpha$: (i) DARK, (ii) BAD COLOR, (iii) OUT OF FOCUS, (iv) BLURRING |
| IMAGE-CAPTURING POSITION ANALYSIS | $\beta$: DIFFERENCE IN SIZE |
| | $\gamma$: DIFFERENCE IN IMAGE-CAPTURING ANGLE |
| | $\delta$: DEVIATION IN IMAGE-CAPTURING POSITION |
| SUBJECT STATE ANALYSIS | $\varepsilon$: RESIDUE EXISTS |
| | $\zeta$: INSUFFICIENT INFLATION OF ORGAN (CONSTRICTION IN SUBMUCOSA) |
| | $\eta$: LESION EXISTS |
| RECORDED-IMAGE ANALYSIS | $\theta$: WHETHER UNCAPTURED IMAGE RELATIVE TO PRE-CAPTURED IMAGE EXISTS OR NOT |
| | $\lambda$: WHETHER DIFFERENCE IN IMAGING ORDER EXISTS RELATIVE TO PRE-CAPTURED IMAGE OR NOT |
| | $\mu$: AUTOMATICALLY RECORD IMAGE WITH SMALLER DIFFERENCE, OR RECORD ALL IMAGES AND AUTOMATICALLY DELETE IMAGES OTHER THAN IMAGE WITH SMALLER DIFFERENCE |

FIG. 7

| | | |
|---|---|---|
| DEVICE RESTRICTION ANALYSIS | SCOPE RESTRICTION ANALYSIS | a: RESTRICTION IS (i) DIAMETER, (ii) BENDING, (iii) LENGTH, (iv) FIELD OF VIEW (DEPTH OF FOCUS, ZOOM, ANGLE OF VIEW) |
| | | b: IN RESTRICTION, (IN VIEW OF CURRENT STATE AND PERFORMANCE) WHETHER ANGLE OPERATION OF FRONT END IS ALLOWED AS SOLUTION, OR TWISTING AND INSERTION/EXTRACTION IS REQUIRED |
| | LIGHT SOURCE RESTRICTION ANALYSIS | c: IN RESTRICTION, WHETHER LIGHT SOURCE TYPE (WHETHER NBI IS ALLOWED) OR LIGHT QUANTITY CAN BE CHANGED |
| | SYSTEM RESTRICTION ANALYSIS | d: COLOR ADJUSTMENT |
| | | e: FRAME RATE, SHUTTER SPEED |
| | | f: STORAGE CAPACITY OR REMAINING CAPACITY |
| IMAGE-CAPTURED PORTION RESTRICTION ANALYSIS | | g: ORGAN RESTRICTION ANALYSIS: (SPACE) WHETHER LUMEN IS WIDE OR NARROW |
| | | h: PORTION STATE RESTRICTION ANALYSIS (SUBMUCOSA STATE): WHETHER PORTION IS ROUGH |
| | | i: CONDITION/APPEARANCE OF RIDGES OF ORGAN |

FIG. 8

| | | |
|---|---|---|
| IMAGE QUALITY CORRECTION | A: CORRECT LIGHT QUANTITY (INCLUDING IMAGE-CAPTURING POSITION) | |
| | B: CORRECT COLOR BALANCE | |
| | C: CORRECT FOCUS (INCLUDING IMAGE-CAPTURING POSITION) | |
| | D: CORRECT FRAME RATE OR SHUTTER SPEED | |
| IMAGE-CAPTURING POSITION CORRECTION | E: PROVIDE GUIDE TO MAKE DISTANCE APPROPRIATE | |
| | F: PROVIDE GUIDE TO MAKE IMAGE-CAPTURING POSITION APPROPRIATE | PROVIDE GUIDE OF ANGLE DEVIATION |
| | | PROVIDE GUIDE OF POSITIONAL DEVIATION |
| | | (PULL ONCE AND) PROVIDE GUIDE TO REAPPROACH |
| SUBJECT STATE CORRECTION | G: PROMPT WATER SENDING | |
| | H: PROMPT AIR SENDING | |
| | I: DISPLAY LESION POSITION | |
| RECORDED-IMAGE CORRECTION | J: DISPLAY EXISTENCE OF UNCAPTURED IMAGE | |
| | K: PROVIDE GUIDE TO PERFORM IMAGE-CAPTURING IN PREDETERMINED IMAGE-CAPTURING ORDER | |
| | L: AUTOMATICALLY RECORD IMAGE WITH SMALLER DIFFERENCE, OR RECORD ALL IMAGES AND AUTOMATICALLY DELETE IMAGES OTHER THAN IMAGE WITH SMALLER DIFFERENCE | |

FIG. 9

| NO. | COMBINATION | OPERATION |
|---|---|---|
| 1 | α(i), c, A | WHEN CAPTURED IMAGE IS DARK, PROVIDE GUIDE OF BRIGHTNESS ADJUSTMENT UNDER RESTRICTION OF LIGHT QUANTITY SETTABILITY AND LIGHT QUANTITY SETTABLE RANGE OF LIGHT SOURCE |
| 2 | α(ii), d, B | WHEN COLOR OF CAPTURED IMAGE IS BAD, ADJUST COLOR UNDER RESTRICTION OF COLOR ADJUSTABLE RANGE OF ENDOSCOPE SYSTEM |
| 3 | α(iii), a(iv), C | WHEN THE CAPTURED IMAGE IS OUT OF FOCUS, ADJUST FIELD OF VIEW UNDER RESTRICTION OF ADJUSTABLE RANGE OF FIELD OF VIEW (DEPTH OF FOCUS, ZOOM, ANGLE OF VIEW) OF ENDOSCOPE SYSTEM |
| 4 | α(iii), AND AT LEAST ONE SELECTED FROM a(i), a(ii) AND g, F | WHEN THE CAPTURED IMAGE IS OUT OF FOCUS, GUIDE IMAGING POSITION IN VIEW OF RESTRICTION OF AT LEAST ONE RESTRICTION OF SCOPE DIAMETER BENDING, LENGTH, AND SIZE OF LUMEN |
| 5 | α(iv), e, D | WHEN CAPTURED IMAGE IS BLURRED, ADJUST FRAME RATE AND SHUTTER SPEED UNDER RESTRICTION OF ADJUSTABLE RANGE OF FRAME RATE AND SHUTTER SPEED OF ENDOSCOPE SYSTEM |
| 6 | β, g, E | WHEN SIZE OF CAPTURED IMAGE IS INAPPROPRIATE, PROVIDE GUIDE TO MAKE IMAGE-CAPTURING DISTANCE APPROPRIATE IN VIEW OF SIZE (AND SHAPE) OF LUMEN |
| 7 | γ, g, F | WHEN IMAGE-CAPTURING ANGLE IS INAPPROPRIATE, GUIDE ENDOSCOPE POSITION AND ANGLE TO MAKE IMAGE-CAPTURING ANGLE APPROPRIATE IN VIEW OF SIZE (AND SHAPE) OF LUMEN |
| 8 | γ, h, F | WHEN IMAGE-CAPTURING POSITION IS INAPPROPRIATE, CONSIDER SUBMUCOSA STATE, AND WHEN SUBMUCOSA IS ROUGH GUIDE IMAGE-CAPTURING POSITION TO PREVENT ENDOSCOPE FROM TOUCHING SUBMUCOSA |
| 9 | δ, g, F | WHEN IMAGE-CAPTURING POSITION IS INAPPROPRIATE, GUIDE ENDOSCOPE POSITION AND ANGLE TO MAKE IMAGE-CAPTURING POSITION APPROPRIATE IN VIEW OF SIZE (AND SHAPE) OF LUMEN |
| 10 | δ, h, F | WHEN IMAGE-CAPTURING ANGLE IS INAPPROPRIATE, CONSIDER SUBMUCOSA STATE, AND WHEN SUBMUCOSA IS ROUGH, GUIDE IMAGE-CAPTURING ANGLE TO PREVENT ENDOSCOPE FROM TOUCHING SUBMUCOSA |
| 11 | ε, g, G | WHEN RESIDUE EXITS, GUIDE WATER SENDING DIRECTION IN VIEW OF SIZE (AND SHAPE) OF LUMEN |
| 12 | ζ, g, H | WHEN INFLATION OF ORGAN IS INSUFFICIENT, IN VIEW OF CONDITION OF WRINKLES OF ORGAN OR APPEARANCE OF RIDGES OF LARGE BOWEL, PROVIDE GUIDE OF NECESSITY OF AIR SENDING OR AIR SENDING AMOUNT |
| 13 | η, c, I | WHEN LESION EXISTS, IN VIEW OF RESTRICTION OF LIGHT SOURCE (WHETHER SPECIAL LIGHT IS ALLOWED) TO DECIDE DISPLAYING ONLY LESION POSITION OR DISPLAYING LESION POSITION TOGETHER WITH MESSAGE PROMPTING SPECIAL LIGHT |
| 14 | θ, b, J | WHEN UNCAPTURED IMAGE EXISTS, CONSIDER WHETHER ANGLE OPERATION OF FRONT END IS ALLOWED AS SOLUTION OR TWISTING OR INSERTION/EXTRACTION IS NECESSARY, AND PROVIDE A GUIDE OF OPERATION FOR CAPTURING UNCAPTURED PORTION |
| 15 | θ, c, L | WHEN UNCAPTURED SPECIAL LIGHT IMAGE EXISTS, CONFIRM RESTRICTION OF LIGHT SOURCE TYPE (WHETHER SPECIAL LIGHT IS ALLOWED) AND DECIDE WHETHER TO PROVIDE GUIDE INCLUDING IMAGE-CAPTURING OF SPECIAL LIGHT IMAGE |
| 16 | λ, b, K | WHEN PERFORMING IMAGE-CAPTURING IN PREDETERMINED IMAGE-CAPTURING ORDER, CONSIDER WHETHER ANGLE OPERATION OF FRONT END IS ALLOWED AS SOLUTION OR TWISTING OR INSERTION/EXTRACTION IS NECESSARY, AND PROVIDE A GUIDE OF OPERATION FOR IMAGE-CAPTURING IN IMAGE-CAPTURING ORDER |
| 17 | μ, f, L | WHEN A PLURALITY OF SIMILAR IMAGES ARE CAPTURED, IN VIEW OF RESTRICTION OF CAPACITY OR REMAINING CAPACITY OF RECORDING SECTION OF ENDOSCOPE SYSTEM, PROVIDE GUIDE WHETHER TO DELETE IMAGES |

ENDOSCOPE APPARATUS, INFORMATION PROCESSING METHOD, AND STORAGE MEDIUM

CROSS REFERENCE TO RELATED APPLICATION

This application is a continuation of International Patent Application No. PCT/JP2020/005077, having an international filing date of Feb. 10, 2020, which designated the United States, the entirety of which is incorporated herein by reference.

BACKGROUND

Known in examination or treatment using an endoscope are techniques for displaying supporting information so as to support an inexperienced user, for example. Japanese Unexamined Patent Application Publication No. 2018-050890 discloses a technique in which a plurality of endoscope images is allocated to corresponding portions of a virtual stomach model to generate a map showing a photographed area and an unphotographed area in order for a doctor to determine unphotographed portions. Furthermore, Japanese Unexamined Patent Application Publication No. 2018-139846 discloses a technique for displaying, on a monitor, operation supporting information for supporting operation of the endoscope in order to acquire inspection images according to a guideline.

SUMMARY

In accordance with one of some aspect, there is provided an endoscope apparatus comprising a processor,
the processor
conducts an analysis whether an endoscope image has been appropriately captured or not on the basis of the endoscope image,
acquires correction restriction information that is at least one of a restriction regarding a size of a lumen of an image-captured portion or a restriction regarding a submucosa state of the image-captured portion, and
generates correction information regarding correction of image-capturing conditions for allowing the endoscope image to be appropriately captured under the restriction of the correction restriction information in a case where it is analyzed that the endoscope image has not been appropriately captured, to output the correction information on a monitor.

In accordance with one of some aspect, there is provided an information processing method that makes a processor:
conduct an analysis whether an endoscope image has been appropriately captured or not on the basis of the endoscope image,
acquire correction restriction information that is at least one of a restriction regarding a size of a lumen of an image-captured portion or a restriction regarding a submucosa state of the image-captured portion, and
generate correction information regarding correction of image-capturing conditions for allowing the endoscope image to be appropriately captured under a restriction of the correction restriction information in a case where it is analyzed that the endoscope image has not been appropriately captured.

In accordance with one of some aspect, there is provided a storage medium storing a program that makes a processor: conduct an analysis whether an endoscope image has been appropriately captured or not on the basis of the endoscope image;
acquire correction restriction information that is at least one of a restriction regarding a size of a lumen of an image-captured portion or a restriction regarding a submucosa state of the image-captured portion; and
generate correction information regarding correction of image-capturing conditions for allowing the endoscope image to be appropriately captured under a restriction of the correction restriction information in a case where it is analyzed that the endoscope image has not been appropriately captured.

BRIEF DESCRIPTION OF THE DRAWINGS

FIG. 6 illustrates an example of analysis items to be analyzed by an appropriate image analysis section.
FIG. 7 illustrates an example of analysis items to be analyzed by a correction restriction information acquisition section.
FIG. 8 illustrates is an example of correction items prescribed by a correction information generation section.
FIG. 9 illustrates combination examples of the items.

DESCRIPTION OF EXEMPLARY EMBODIMENTS

Figure 1:
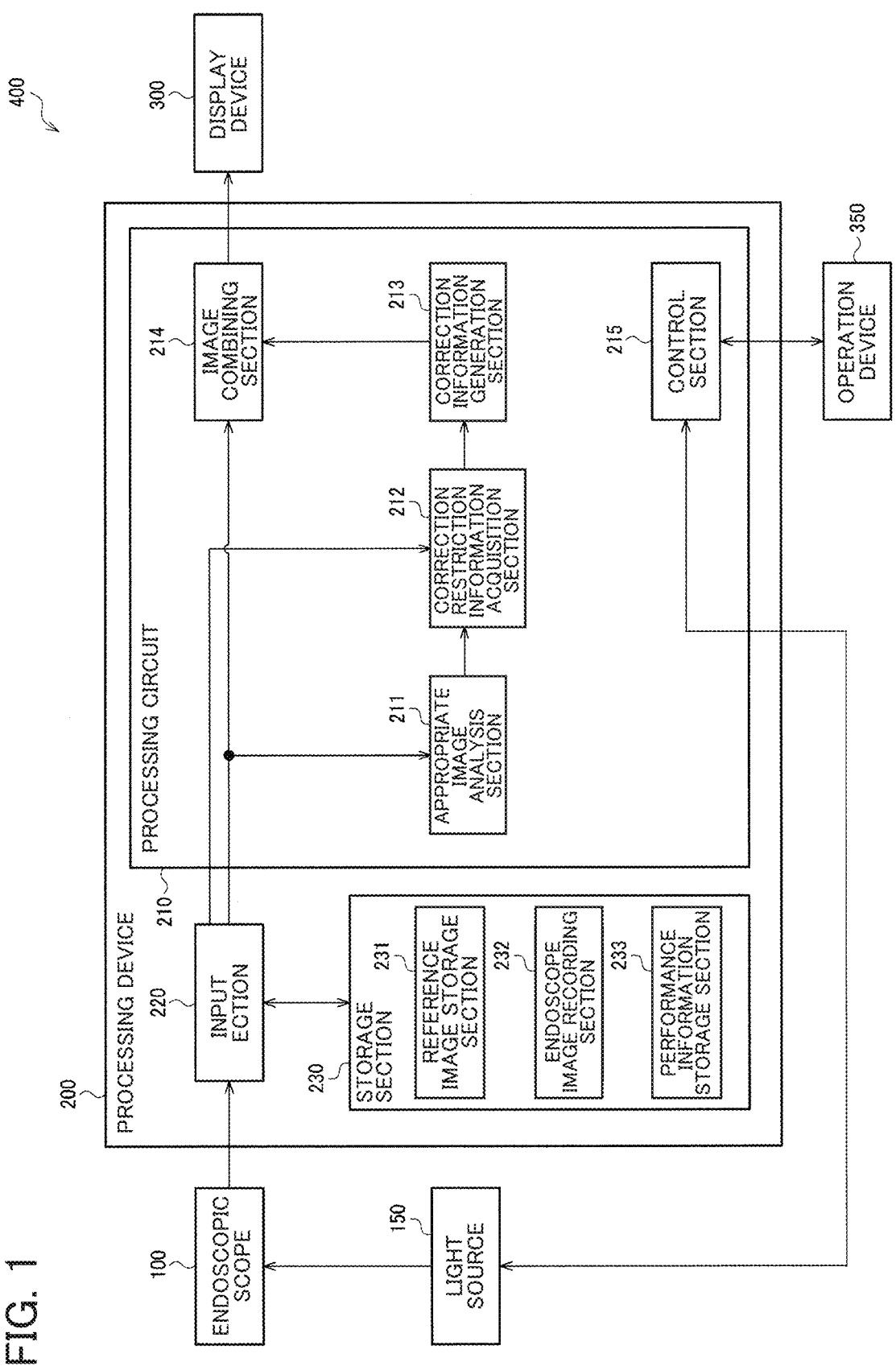
FIG. 1 illustrates a first configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

Hereinafter, an upper digestive tract examination using a medical endoscope will be described as an example. However, application targets of contents of this disclosure are not limited to an upper digestive tract endoscope. The contents of this disclosure may be applied to a lower digestive tract endoscope, a surgical endoscope, or an industrial endoscope.

1. First Configuration Example

FIG. 1 illustrates a first configuration example of an endoscope apparatus 400. The endoscope apparatus 400 includes an endoscopic scope 100, a light source 150, a processing device 200, a display device 300, and an operation device 350.

The endoscopic scope 100 has a long narrow shape to allow insertion into the body, and has one end provided with an imaging lens, an imaging sensor, an illumination lens, and the like. The other end of the endoscopic scope 100 is provided with a connector detachable to and from the processing device 200. In the case of the endoscopic scope 100 as a flexible scope, a scope front end is configured bendably and an angle of the scope front end is operated by a dial or the like. Performance of the scope, such as a radius of bending, the maximum angle, a diameter of the scope front end, a type of the imaging sensor, an imaging frame rate, a zoom magnification, and an angle of view, is determined depending on models of the scope.

The light source 150 generates illumination light for illuminating an image-captured portion. The light source 150 includes a light emitting element, an optical system that makes light emitted by the light emitting element enter a light guide of the endoscopic scope 100, and a driving circuit that drives the light emitting element. The light source 150 may further include an optical filter that changes a type of the illumination light. The light emitting element is a xenon lamp, a light emitting diode (LED), or a laser diode, for example. Various types of the illumination light, i.e., various spectral characteristics of the illumination light may be adopted. It is also possible to adopt a configuration that allows a plurality of spectral characteristics to be switched in accordance with observation modes. For example, the observation mode may be switched in response to operation input from the operation device 350. For example, the endoscope apparatus 400 may have a normal light mode and a special light mode as an illumination light mode. The normal light mode is a mode for acquiring a white light image, and the special light mode is a mode for acquiring a special light image, i.e., a non-white light image. Various modes can be assumed as the special light mode, examples of which are an observation mode using narrowband light, and an observation mode using fluorescent of a tissue or a medical agent. Performance of the light source 150 such as a type of the illumination light that the light source 150 can emit, adjustability/inadjustability of light quantity, an adjustable range of the light quantity, and a light distribution characteristic of the illumination light is determined depending on models of the light source.

The display device 300 displays an image output from the processing device 200. The display device 300 is also called monitor, which is a liquid crystal display or an electro-luminescence (EL) display, for example.

The operation device 350 is a device for performing operation input to the endoscope apparatus 400. The operation device 350 may include a button, a dial, a switch, a foot pedal, a touch panel, a mouse, or a keyboard, for example.

The processing device 200 performs image processing, and control of the endoscope apparatus 400. The processing device 200 includes a processing circuit 210, an input section 220, and a storage section 230.

The storage section 230 stores images and various types of information. Specifically, the storage section 230 includes an endoscope image recording section 232. In the case where a reference image is used to generate operation supporting information, the storage section 230 may further include a reference image storage section 231. In the case where performance information of the endoscope apparatus 400 is saved in the processing device 200, the storage section 230 may further include a performance information storage section 233. An example of the storage section 230 is a semiconductor memory, a magnetic storage device, an optical storage device, or the like. An example of the semiconductor memory is a RAM, a non-volatile memory, or the like. The reference image storage section 231, the endoscope image recording section 232, and the performance information storage section 233 may be individually-provided separate storage devices, or may be separate storage sections provided in a single storage device.

The endoscope image recording section 232 records endoscope images captured by the endo scope apparatus 400. The endos cope images represent frame images in a still image or a movie, and the still image or the movie is recorded in the endoscope image recording section 232.

The reference image storage section 231 stores one or a plurality of reference images to be used as a criterion in generation of the operation supporting information. The reference image is a criterion used in inspection, diagnosis, or treatment whose operation is to be supported for determining whether an image has been appropriately captured or not. For example, in the case of inspection, diagnosis, or treatment provided with a guideline in which an image to be captured is presented, the image appropriately captured in accordance with the guideline is stored in the reference image storage section 231 as a reference image. Furthermore, when an image-capturing order of the images is presented in the guideline, the image-capturing order may be stored in the reference image storage section 231 together with the reference image.

The performance information storage section 233 stores performance information of the endoscope apparatus 400. The performance information is information showing performance of devices included in the endoscope apparatus 400. The performance of a device is exemplified by a shape or size of the device, operation of the device, an adjustable range of operation or processing, a function of the device, or the like. An example of the performance information is the above-mentioned performance of the endoscopic scope 100 and the light source 150. Note that the performance information may be stored in memories (not illustrated) respectively provided in the endoscopic scope 100 and the light source 150, and the stored performance information may be input to the processing circuit 210. In such configuration, the performance information storage section 233 may be omitted.

The input section 220 inputs endoscope images to the processing circuit 210. The input section 220 is an image interface that receives an image-capturing signal from the endoscopic scope 100 or an access control circuit that reads recorded images from the endoscope image recording section 232, or both of the image interface and the access control circuit. The image interface performs processing of constituting an image from the received image-capturing signal and outputs the constituted image to the processing circuit 210 as an endoscope image. The access control circuit records the endoscope image in the endoscope image recording section 232. The access control circuit reads the endoscope image recorded in the endoscope image recording section 232 and outputs the read endoscope image to the processing circuit 210. Hereinafter, the endoscope image may represent any one of a real-time image generated by the input section 220 on the basis of the image signal from the endoscopic scope 100 or a recorded image read by the input section 220 from the storage section 230.

Furthermore, the input section 220 may input the reference image, the performance information, or both of the reference image and the performance information to the processing circuit 210. Specifically, the access control circuit reads the reference image from the reference image storage section 231 and outputs the read reference image to the processing circuit 210. Furthermore, the access control circuit reads the performance information from the performance information storage section 233 and inputs the read reference information to the processing circuit 210.

The processing circuit 210 performs image processing and control processing. The processing circuit 210 includes an appropriate image analysis section 211, a correction restriction information acquisition section 212, a correction information generation section 213, an image combining section 214, and a control section 215. The processing circuit 210 is configured by one or a plurality of circuit components. For example, the processing circuit 210 is configured by a processor, an FPGA, an ASIC, and/or the like. Each section of the processing circuit 210 may be configured by a separate circuit. Alternatively, the processing circuit 210 may be configured by a processor. In the latter configuration, the processor executes a program describing operation of the sections of the processing circuit 210 to implement the operation of the sections. The processor is a CPU, a microcomputer, a DSP, or the like.

The appropriate image analysis section 211 conducts analysis whether the endoscope image has been appropriately captured or not on the basis of the endoscope image input from the input section 220, and outputs a result of the analysis to the correction restriction information acquisition section 212.

An appropriate image is an image having quality or contents suitable for observing the endoscope image, more specifically, an image satisfying a predetermined criterion. A criterion for the quality is exemplified by brightness of the image, noises of the image, movements in the image, or the like. A criterion for the contents is exemplified by an image-captured portion, an image-capturing order, an image-capturing position, an image-capturing angle, a size of an image-captured portion in the image, a state of the image-captured portion, or the like. One or more of the criteria may be used in combination.

The correction restriction information acquisition section 212 acquires, on the basis of the result of the analysis performed by the appropriate image analysis section 211, correction restriction information, which is at least one of a restriction based on an endoscope device or a restriction based on the image-captured portion at the time of changing image-capturing conditions of the endoscope image, and outputs the acquired correction restriction information to the correction information generation section 213. The correction restriction information acquisition section 212 additionally uses the performance information of the endoscope apparatus 400 in a case where correction restriction information based on the endoscope device is acquired.

The image-capturing conditions represent conditions about image-capturing of the endoscope image, more specifically, conditions having some influence on the quality or contents of the endoscope image by being changed. For example, the image-capturing conditions are an image-capturing position, the image-capturing angle, the angle of view, and the like of the endoscopic scope 100. Alternatively, the image-capturing conditions are light quantity of the illumination light, a type of the illumination light, and the like. The type of the illumination light is namely a light distribution characteristic of the illumination light. Alternatively, the image-capturing conditions are a frame rate, a shutter speed, an aperture stop status, sensitivity, a zoom magnification, and the like of image-capturing.

The restriction means that some restriction prevents implementation of a change to be made in image-capturing conditions for correcting the endoscope image to an appropriate image.

The restriction based on the endoscope device is a restriction caused by performance of the device. For example, operation is restricted due to a shape or size of the device, operation of the device or operation beyond the adjustable range of motion is restricted, and operation is restricted by a lack in the device of a function that implements certain operation.

The restriction based on the image-captured portion is a restriction caused by a feature of the image-captured portion. The feature of the image-captured portion is exemplified by a shape, a size, a state, or the like of the image-captured portion. For example, operation is restricted due to the shape or size of the image-captured portion or image-capturing of the appropriate image is restricted due to the state of the image-captured portion. When the latter restriction is specifically a state of the image-captured portion that cannot possibly provide an appropriate image even when being captured, the appropriate image cannot be obtained even when scope operation or image-capturing is performed unless operation for improving such state of the image-captured portion is performed.

The correction restriction information is information showing presence/absence or details of the restriction. Specifically, the correction restriction information represents what kind of image-capturing condition is changed by the restriction, whether or not the image-capturing conditions can be changed under the restriction, or details of the restriction.

When it is analyzed that the endoscope image has not been appropriately captured, the correction information generation section 213 generates correction information on correction of the image-capturing conditions for performing appropriate image-capturing under the restriction of the correction restriction information, and outputs the generated correction information to the image combining section 214. Note that as described later referring to FIG. 10, when the correction information is used for internal control of the endoscope apparatus 400, the correction information generation section 213 may output the correction information to the control section 215.

The correction information is information indicating image-capturing conditions to be corrected, and information indicating how to correct the image-capturing conditions. Furthermore, the correction information may be information indicating an operation method for correcting the image-capturing conditions.

The image combining section 214 combines the correction information with the endoscope image input from the input section 220, and outputs the combined endoscope image to the display device 300. The display device 300 displays an image from the image combining section 214. The image presents a user correction information provided in view of the restriction. For example, the correction information contains text or an image, and the image combining section 214 combines the text or the image with the endoscope image to generate a display image. For example, the display image is divided into two areas, one of which displays the endoscope image and the other of which displays the correction information. Alternatively, the correction information is superimposed on the endoscope image.

Note that FIG. 1 illustrates an example of the processing circuit 210 including the image combining section 214, but a presentation method of the correction information is not limited to the example of FIG. 1. The processing circuit 210 may include a presentation section that presents the correction information to the user. The image combining section 214 is one example of the presentation section. Alternatively, the presentation section may use a voice to present the correction information to the user.

Operation of endoscopes is sometimes restricted by various factors. For example, a restriction due to structure or performance of the endoscope device, a restriction due to structure or a state of the image-captured portion, or the like is assumed. Even when supporting information for supporting operation of the endoscope is displayed, the operation may not be executed as long as the operation is limited by a restriction.

According to the embodiment described above, correction restriction information at the time of changing the image-capturing conditions of the endoscope image is acquired, and the correction information related to correction of the image-capturing conditions is generated on the basis of the acquired correction restriction information. As a result, it is possible to present the user the correction information provided in view of the restriction at the time of changing the image-capturing conditions. Specifically, correction operation that can be implemented under the restriction can be presented to the user. Alternatively, it is possible to present the user that the correction operation is unfeasible under the restriction under the current condition. As a result, effective support can be provided to the user so as to enable image-capturing of appropriate images in examination or treatment using an endoscope. For example, when a restriction is not considered and unfeasible operation is presented, the user is required to determine that the presented operation is unfeasible. According to this embodiment, such determination is unnecessary because the restriction has been taken into consideration. As a result, effective support is provided to, for example, an unskilled doctor.

The endoscope apparatus 400 according to this embodiment is applicable to various types of examination or treatment, and one example of assumed application is stomach examination using an endoscope. In the stomach examination using an endoscope, a secondary examination is performed using recorded images of a primary examination. The primary examination corresponds to image-capturing and recording portions by an endoscope, and the secondary examination corresponds to observing the images to make a diagnosis. Accordingly, the primary examination in the stomach examination requires completely recording necessary spots. However, a doctor who performs the primary examination is not always a doctor skilled in operating endoscopes and it is desirable that the doctor who performs the primary examination can receive support. In this embodiment, it is possible to provide effective support taking the restriction into consideration even when a doctor not skilled in operating endoscopes performs the primary examination.

2. Detailed Configuration and Operation

Description will be made to detailed configuration and operation of the above-mentioned first configuration example. Hereinafter, the stomach examination is described as an example. However, application targets of the endoscope apparatus 400 are not limited to the stomach examination. Although acquisition of an image in accordance with a guideline is hereinafter described as an example, the endoscope apparatus 400 is also applicable to examination or treatment performed without the guideline. When the guideline is not used, criteria such as reference images to be captured and an image-capturing order of the reference images, for example, are consequently not used.

Figure 2:
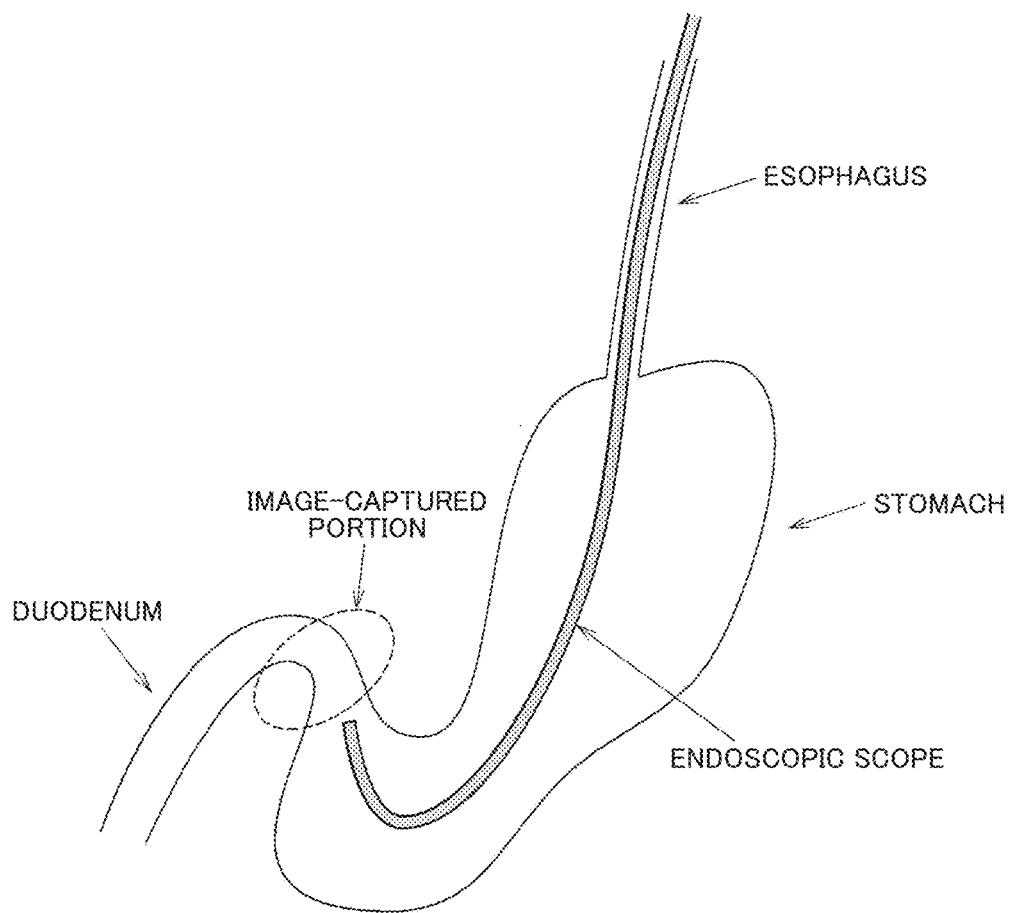
FIG. 2 is a diagram illustrating a stomach examination using an endoscope.

FIG. 2 is a diagram illustrating a stomach examination performed using an endoscope. In a primary examination of the stomach examination, firstly an endoscopic scope is inserted into the duodenum. After that, the endoscopic scope is returned from the duodenum through the stomach and the esophagus in this order while image-capturing predetermined portions. The portions to be photographed and the image-capturing order of the portions are defined in a guideline. The duodenum, the stomach, and the esophagus respectively have portions divided as a plurality of examination portions. At the respective examination portions, one or a plurality of images are captured, and approximately forty images are captured in total. When such prescribed images are to be captured, the image-captured portions for the endoscopic scope correspond to portions to be captured defined in the guideline.

Figure 3:
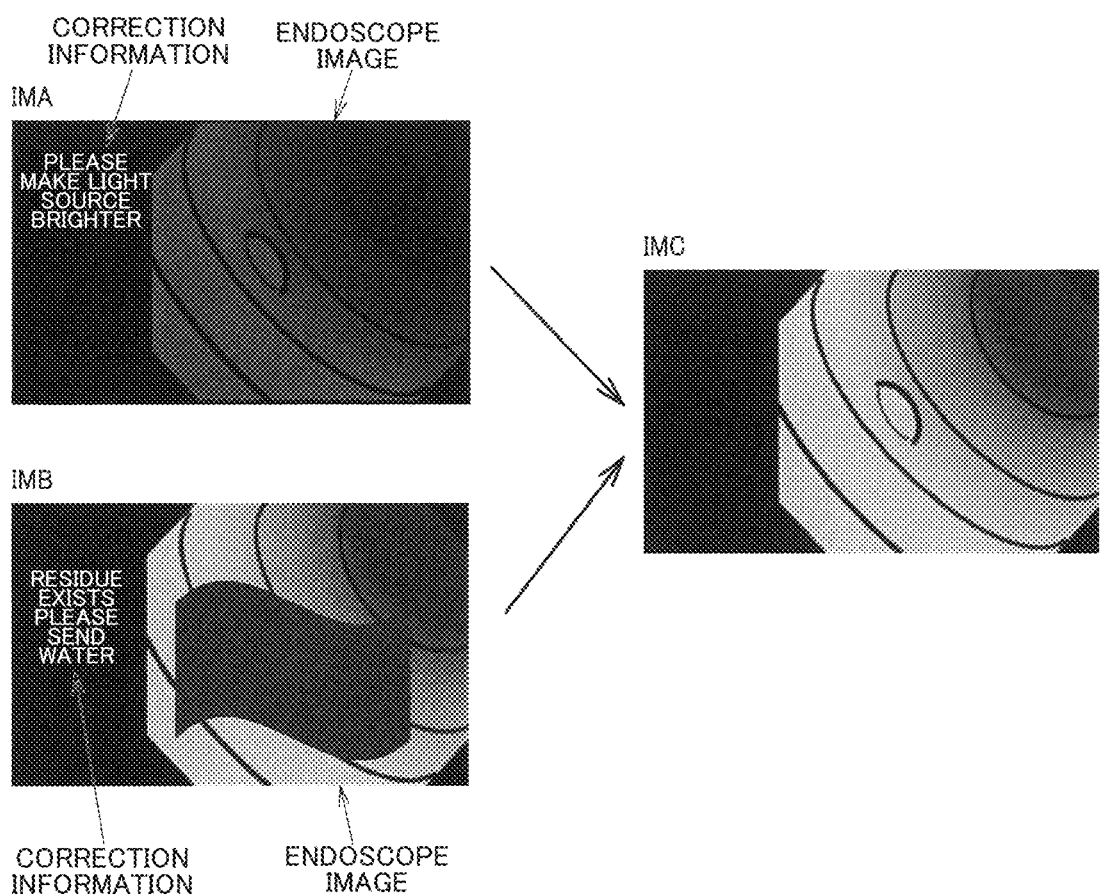
FIG. 3 is a diagram illustrating operation of the endoscope apparatus.

FIG. 3 is a diagram illustrating operation of the endoscope apparatus 400. Note that description here is made to an example of the correction information, and detailed examples will be described later. Images IMA to IMC, which are separate images respectively displayed at different timings, are illustrated in a single drawing for convenience.

The image IMA is an example of correction information presented when the endoscope image is dark. Specifically, when the appropriate image analysis section 211 determines that the endoscope image is dark, the correction restriction information acquisition section 212 determines whether the light quantity of the light source can be adjusted to appropriate light quantity. When the restriction information acquisition section 212 determines that the light quantity of the light source is adjustable to the appropriate light quantity, the correction information generation section 213 generates correction information on light quantity adjustment and the image combining section 214 combines a message "Please make the light source brighter." with the endoscope image.

The image IMB is an example of the correction information presented when a residue exists in the image-captured portion. Specifically, when the appropriate image analysis section 211 determines that the endoscope image has a residue captured therein, the correction restriction information acquisition section 212 determines whether the endoscopic scope has a water-sending function. When the correction restriction information acquisition section 212 determines that the endoscopic scope has the water-sending function, the correction information generation section 213 generates correction information on a water-sending operation and the image combining section 214 combines a message "A residue remains. Please send water." with the endoscope image.

When the user adjusts the light quantity or sends water according to the correction information, the appropriate image IMC can be captured. The correction information presented to the user is operation determined as feasible under the restriction, and therefore the user can be provided with appropriate operation support.

Figure 4:
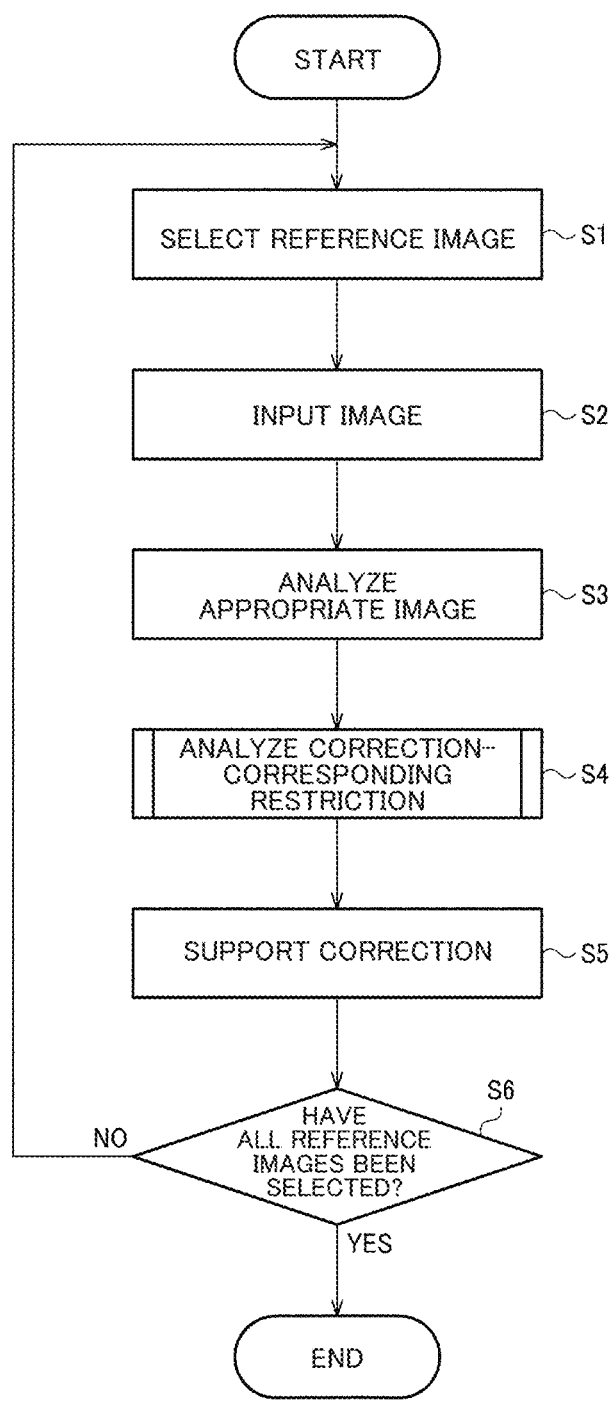
FIG. 4 is a flowchart illustrating a procedure of generating correction information.

FIG. 4 is a flowchart illustrating a procedure of generating correction information. In step S1, the appropriate image analysis section 211 follows a specified image-capturing order to select one reference image from a plurality of reference images. In step S2, the input section 220 inputs the endoscope image to the processing circuit 210.

In step S3, the appropriate image analysis section 211 determines whether the endoscope image satisfies a criterion to analyze whether the endoscope image has been appropriately captured. Here, whether the image is appropriate or not is based on a plurality of determination criteria. The appropriate image analysis section 211 notifies the correction restriction information acquisition section 212 of a criterion that has not been satisfied by the endoscope image among the plurality of criteria.

In step S4, the correction restriction information acquisition section 212 determines the correction method on the basis of the result of analysis performed by the appropriate image analysis section 211, analyzes the restriction regarding the correction method, and acquires the correction restriction information. The correction method is a method for correcting the image-capturing conditions so as to make the endoscope image determined to not satisfy the criterion satisfy the criterion. The correction restriction information acquisition section 212 outputs the analysis result as the correction restriction information to the correction information generation section 213.

In step S5, the correction information generation section 213 generates the correction information based on the correction restriction information. When the correction restriction information indicates no-restriction, the correction information generation section 213 generates correction information for instructing a correction method having no restriction. When the correction restriction information indicates there is a restriction, the correction information generation section 213 generates correction information based on the correction restriction information. Specifically, the correction information generation section 213 generates correction information for instructing a correction method other than a correction method having a restriction, or generates correction information presenting the correction method having a restriction along with the fact that the correction method has a restriction.

In step S6, the appropriate image analysis section 211 determines whether all of the reference images have been selected or not, and terminates the process when all of the reference images have been selected. When an unselected reference image exists, the appropriate image analysis section 211 returns to step 51 and selects a next reference image.

Figure 5:
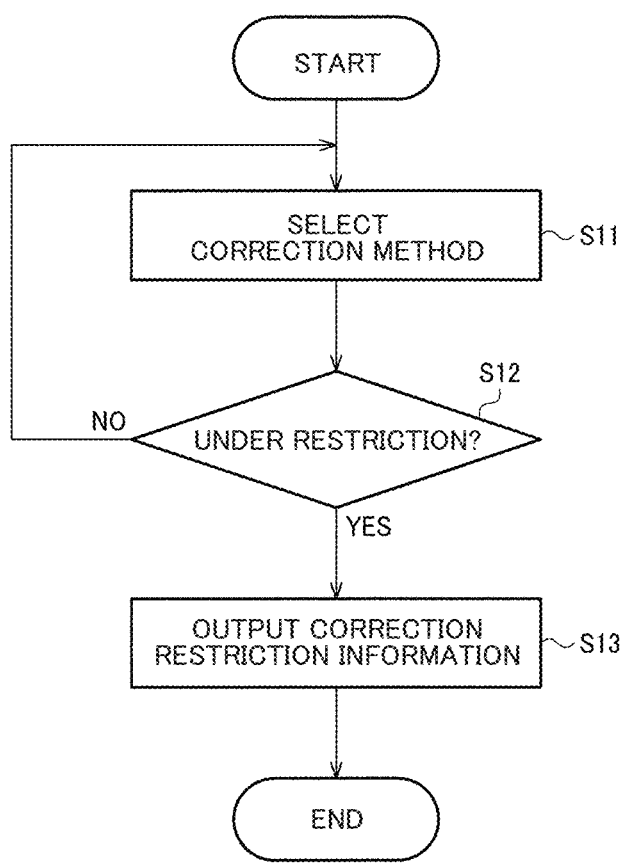
FIG. 5 is a flowchart illustrating a detailed procedure of correction-corresponding restriction analysis.

FIG. 5 is a flowchart illustrating a detailed procedure of the correction-corresponding restriction analysis in step S4. This procedure is described on the premise that the correction method for correcting the endoscope image to satisfy the criterion is selected from one or a plurality of options. The options of the correction method vary depending on the type of the unsatisfied criterion. When there is a plurality of options, the options may be numbered in order from, for example, the one with the easiest operation.

In step S11, the correction restriction information acquisition section 212 selects one correction method from one or a plurality of correction methods regarding the criterion determined in step S3 as not being satisfied. When the plurality of criteria is denoted with order numbers, the correction method may be selected in accordance with the order numbers.

In step S12, the correction restriction information acquisition section 212 analyzes whether the correction method to be selected is feasible under the restriction. When the correction method is infeasible under the restriction, the correction restriction information acquisition section 212 returns to step S11 and selects a next correction method.

When the correction method is feasible under the restriction, the correction restriction information acquisition section 212 outputs in step S13 correction restriction information indicating that the correction method is feasible under the restriction.

When the correction method is infeasible under the restriction in step S12, the correction restriction information acquisition section 212 may not return to step S11 and may proceed to step S13 to output correction restriction information indicating that the correction method is not feasible under the restriction.

FIG. 6 to FIG. 9 are diagrams illustrating detailed operation of the appropriate image analysis section 211, the correction restriction information acquisition section 212, and the correction information generation section 213.

FIG. 6 illustrates an example of analysis items to be analyzed by the appropriate image analysis section 211. Listed in FIG. 6 are ten analysis items, one of which or a plurality of which may be subjected to analysis executed by the appropriate image analysis section 211.

In image quality analysis, quality of the endoscope image is analyzed. The image quality analysis includes an item a to be analyzed, and the item a further includes sub-items (i) to (iv).

In the item (i), determination is made whether the endoscope image is dark or not. Brightness of the image can be calculated through various methods. For example, average luminance in the image may be calculated, and the calculated average luminance may be compared with reference luminance. Alternatively, luminance of a region of interest in the image may be calculated, and the calculated luminance may be compared with the reference luminance.

In the item (ii), determination is made whether the endoscope image has good color or not. The color to be subjected to determination may be a color balance of the entire image, a color balance of the region of interest, or a color tone of a specific tissue such as a submucosa. The color balance is, for example, a white balance of the image, and the white balance of the image is compared with a reference white balance. The color tone is, for example, a hue of the image, and the hue of the image is compared with a reference hue.

In the item (iii), determination is made whether the endoscope image is in focus or not. The determination may be made to a focus on the entire endoscope image, a focus on the region of interest, or presence/absence of an in-focus region in the image. For example, the endoscope image is subjected to high-pass filtering to obtain a contrast value calculated, and the contrast value and a reference contrast value are compared with each other.

In the item (iv), determination is made to blurring of the endoscope image. The blurring can be determined by the contrast value similarly to the item (iii), for example.

In image-capturing position analysis, a difference in the image-capturing position between the reference image captured in advance and the endoscope image is analyzed. The image-capturing position analysis includes items β, γ, and δ to be analyzed.

In the item β, determination is made whether the image-captured portion on the image has a difference in size or not. The size of the image-captured portion means a dimension or an interval of ridges of the submucosa, a dimension of uneven structure, or a dimension of luminal structure. The difference in size of the image-captured portion on the image means that a distance between the front end of the endoscopic scope and the image-captured portion has a difference.

In the item γ, determination is made whether there is a difference in image-capturing angle. The image-capturing angle is an angle formed between an optical axis of the endoscopic scope and the image-captured portion when the image is captured. The image-capturing angle is determined by a direction of the ridges, an angle of the uneven structure, a direction of the luminal structure, or the like.

In the item δ, determination is made whether the image-captured portion on the image is deviated in position. For example, determination is made whether the image-captured portion that should appear in the center of the image appears in the center in the endoscope image or not. The position of the image-captured portion may be determined, for example, by a position of a characteristic point extracted through characteristic point extraction, or may be determined through a matching process between the reference image and the endoscope image.

In subject state analysis, a state of the image-captured portion appearing in the endoscope image is analyzed. The subject state analysis includes items ε, ζ, and η to be analyzed.

In the item ε, determination is made whether there is a residue in the image-captured portion or not. The residue is the one that should have been essentially eliminated but remains without being eliminated. That is to say, when the residue exists, the submucosa, which should essentially appear in the image, does not appear because being blocked behind the residue. The determination as the residue is made for example by whether a region having a different color with a color of the reference image exists in the endoscope image, whether a region having a color of the residue, if known, exists in the endoscope image, or the like.

In the item ζ, determination is made whether an organ containing the image-captured portion is sufficiently inflated. In examination using an endoscope, a lumen of an organ is inflated through insufflation, and analysis is conducted whether a degree of inflation is appropriate or not. For example, insufficient inflation leads to constriction of the submucosa and makes the ridges deeper, and therefore the state of the ridges is used to determine the degree of inflation. Alternatively, the degree of inflation may be determined from a size of inflated uneven structure or the lumen.

In the item η, determination is made whether there is a lesion in the image-captured portion. The lesion is, for example, a cancer, a polyp, an inflammation, bleeding, or the like. As a method to detect lesions, various known methods can be adopted. For example, determination may be made whether a blood vessel or structure of a submucosa has a typical pattern of a lesion, or determination as a lesion may be made on the basis a typical color of the lesion.

In recorded-image analysis, analysis is conducted as to a difference between a plurality of reference images captured in advance and a plurality of endoscope images captured and recorded in correspondence with the reference images. The recorded-image analysis includes items θ, λ, and μ to be analyzed.

In the item θ, determination is made whether there is an uncaptured image. That is to say, determination is made whether all of the endoscope images respectively corresponding to the plurality of reference images are captured or not.

In the item λ, determination is made whether there is a difference in an image-capturing order. That is to say, the plurality of reference images has an image-capturing order defined, and determination is made whether the plurality of endoscope images is captured in the defined image-capturing order.

In the item μ, the endoscope image is selected on the basis of the reference image. Specifically, among a series of endoscope images captured as a movie or the like, an endoscope image having a smaller difference from the reference image is automatically recorded. Alternatively, a series of endoscope images captured as a movie or the like is recorded, and, among the recorded endoscope images, images other than the endoscope image having a smaller difference from the reference image is automatically deleted. The difference between the reference image and the endoscope image is determined on the basis of one or a plurality of items among the items α to λ, for example.

FIG. 7 is an example of analysis items to be analyzed by the correction restriction information acquisition section 212. Listed in FIG. 7 are nine analysis items, one of which or a plurality of which may be subjected to analysis executed by the correction restriction information acquisition section 212.

In device restriction analysis, analysis is conducted as to restrictions of devices provided in the endoscope system. The device restriction analysis includes scope restriction analysis of analyzing a restriction of the scope, light source restriction analysis of analyzing a restriction of the light source, and system restriction analysis of analyzing a restriction of the system.

The scope restriction analysis includes items a and b to be analyzed. The item a further includes sub-items (i) to (iv).

In the item (i), a restriction by a scope diameter is analyzed. That is to say, determination is made, when a scope operation is to be performed for correcting the image-capturing conditions, whether the scope operation is restricted by the scope diameter. The scope diameter is predetermined depending on a model of the scope. For example, a size of a lumen, a concave portion, a ridge inside, or the like is compared with the scope diameter, and determination is made whether the scope can be inserted into the lumen, the concave portion, the ridge inside, or the like.

In the item (ii), analysis is conducted as to a restriction in an angle operation of a scope bending section. That is to say, determination is made, when the angle operation is to be performed for correcting the image-capturing conditions, whether such correction is possible under the restriction of the angle operation or not. Determination whether the correction is possible under the restriction is made on the basis of a current angle, an adjustable angle range, and angle adjustment required for correction. For example, when the angle operation is performed through a dial operation, a sensor that measures a dial rotation amount is provided, and an output value from the sensor indicates the current angle. The adjustable angle range is predetermined depending on a model of the scope. The angle adjustment required for correction can be recognized by the analysis of the image-capturing angle similarly to the item γ of FIG. 6, for example.

In the item (iii), a restriction by a scope length is analyzed. That is to say, determination is made, when scope insertion/extraction is to be performed for correcting the image-capturing conditions, whether the insertion/extraction is restricted by the scope length or not. Determination whether the correction is possible under the restriction is made on the basis of a current insertion length, a length of the scope insertion section, and an insertion/extraction amount required for correction. The length of the scope insertion section is predetermined depending on a model of the scope. The insertion/extraction amount required for correction can be recognized by the analysis of the image-capturing position similarly to, for example, the item δ of FIG. 6. The current insertion length can be measured using a conventional method. For example, magnetic sensors may be added in a mouth piece held in a patient's mouth and a scope section to calculate a movement amount, or an acceleration sensor may be provided in the vicinity of the image-captured portion for the scope to calculate the movement amount from the insertion section (mouth).

In the item (iv), a restriction by a field of view of the scope is analyzed. The field of view includes at least one of a depth of focus, a zoom magnification, and an angle of view. Determination is made, when scope operation is to be performed for correcting the image-capturing conditions, whether the scope operation is restricted by the field of view or not. The depth of focus, the zoom magnification, and the angle of view are predetermined depending on a type of the scope. Specifically, determination is made, when the scope is moved to correct the image-capturing conditions or the like, whether the correction within the depth of focus or the angle of view is possible or not. That is to say, determination is made whether such correction of the scope position is possible that allows a desired image-capturing range to be kept within the range of the depth of focus or the angle of view. Alternatively, determination is made, when the dimension of the image-captured portion on the image or the image-capturing range is corrected, whether such correction within the adjustable range of the zoom magnitude is possible or not. That is to say, determination is made whether adjustment of the zoom magnitude leads to the desired image-capturing range kept within the field of view or not.

The light source restriction analysis includes an item c to be analyzed.

In the item c, a restriction by the type of light source or the light quantity is analyzed. That is to say, determination is made, when the type of the light source or the light quantity is to be changed for correcting the image-capturing conditions, whether such change in the type of light source or the light quantity is possible or not. Specifically, determination is made, when switching to an observation mode such as a special light mode is to be performed, whether setting of the observation mode is applicable to the light source or not. Alternatively, determination is made, when the light quantity is to be adjusted for correcting the brightness of the image, whether such adjustment of the light quantity is possible within a light quantity settable range of the light source. This determination is based on the current light quantity, the light quantity settable range, and an adjustment amount required for correction. The current light quantity is determined from a control signal or the like of the light source. The light quantity settable range is predetermined depending on a model of the light source. The adjustment range required for correction is determined from the luminance of the image similarly to the item α(i) of FIG. 6, for example.

The system restriction analysis includes items d to f to be analyzed.

In the item (d), a restriction by a color adjustable range of the endoscope system is analyzed. That is to say, determination is made, when the color of the endoscope image is to be corrected for correcting the image-capturing conditions, whether such correction of the color is possible under the restriction or not. The color adjustable range is an adjustment range defined depending on one of or both of the type of settable illumination light and a color adjustment range through image processing. Determination whether correction under the restriction is possible or not is made on the basis of a current color of the image, a color adjustable range, and an adjustment amount required for correction. The current color of the image is acquired by calculating the white balance, hue, or the like. The color adjustable range is predetermined depending on a model of the light source or a processing device. The adjustment range required for correction is determined from the color of the image similarly to the item α(ii) of FIG. 6, for example.

In the item e, a restriction by an adjustable range of a frame rate or a shutter speed of the endoscope system is analyzed. That is to say, determination is made, when the frame rate or the shutter speed is to be corrected for correcting the image-capturing conditions, whether such correction of the frame rate or the shutter speed is possible under the restriction. Determination whether correction is possible under the restriction or not is made on the basis of a current frame rate or a shutter speed, an adjustable range of the frame rate or the shutter speed, and an adjustment amount required for correction. The current frame rate or the shutter speed is acquired on the basis of a image-capturing control signal or the like. The adjustable range is predetermined depending on a model of the endoscopic scope. The adjustment range required for correction is determined for example from the brightness of the image, blurring, or the like.

In image-captured portion restriction analysis, a restriction by the image-captured portion is analyzed. The image-captured portion restriction analysis includes items g to i to be analyzed.

In the item g, a restriction by an organ containing the image-captured portion is analyzed. That is to say, determination is made, when the scope is to be operated for correcting the image-capturing conditions, whether such operation of the scope is possible under the restriction of the organ or not. Specifically, determination is made on the basis of the size of the organ lumen whether the scope operation required for correction can be implemented within a space of the lumen. The size of the lumen is acquired on the basis of the endoscope image, for example.

In the item h, a restriction by the state of the image-captured portion is analyzed. That is to say, determination is made whether the state of the image-captured portion satisfies a criterion or not. Specifically, determination is made whether a submucosa state of the image-captured portion satisfies the criterion or not. The submucosa state is roughness of the submucosa, for example. The submucosa state is determined, for example, on the basis of the endoscope image from the color, structure, or the like of the submucosa.

In the item i, a restriction by a condition of ridges of the organ containing the image-captured portion or an appearance of the ridges is analyzed. Specifically, determination is made, whether the condition or appearance of the ridges satisfies the criterion or not, or, when the scope is to be operated for correcting the image-capturing conditions, whether such operation of the scope is possible under the restriction by the condition or the appearance of the ridges. As the condition or appearance of the ridges, information is acquired on the basis of, for example, the endoscope image, the information including a size, an interval, a depth of the ridges, or existence of a ridge inside.

FIG. 8 is an example of correction items prescribed by the correction information generation section 213. Listed in FIG. 8 are twelve correction items, correction information may be generated to one of which or a plurality of which by the correction information generation section 213.

In image quality correction, correction information for correcting quality of the endoscope image is generated. The image quality correction includes items A, B, C, and D to be corrected.

In the item A, correction information for correcting light quantity is generated. Specifically, generated is correction information for correcting brightness of the endoscope image by correcting an amount of light to be emitted from the light source, or correction information for correcting brightness of the endoscope image by changing a distance between the endoscopic scope and the image-captured portion.

In the item B, correction information for correcting a color balance is generated. Specifically, generated is correction information for changing a type of the illumination light, correction information for changing setting of a white balance in the image processing, or correction information for changing setting of a hue in the image processing.

In the item C, correction information for correcting a focus is generated. Specifically, generated is correction information for correcting the focus by an automatic focus function or a manual focus function of the endoscopic scope, or correction information for correcting the focus by changing a distance between the endoscopic scope and the image-captured portion.

In the item D, correction information for correcting the frame rate or the shutter speed is generated. Specifically, in the case of an endoscopic scope to which a setting of a plurality of frame rates is applicable, correction information for changing the setting of the frame rate is generated. Alternatively, in the case of an endoscopic scope to which a setting of a plurality of shutter speeds is applicable, correction information for changing the setting of the shutter speed is generated.

In image-capturing position correction, correction information for correcting a difference in the image-capturing position between the reference image captured in advance and the endoscope image is generated. The image-capturing position correction includes items E and F to be corrected.

Generated in the item E is correction information for providing a guide to make a distance between the endoscopic scope and the image-captured portion appropriate.

Generated in the item F is correction information for providing a guide to make the image-capturing position of the endoscopic scope appropriate relative to the image-captured portion. Specifically, generated is correction information for providing a guide to make an image-capturing angle appropriate, correction information for providing a guide to make a position of the image-captured portion in the endoscope image appropriate, or correction information for providing a guide to make the endoscopic scope re-approach the image-captured portion after being pulled once.

In subject state correction, correction information for correcting the state of the image-captured portion appearing in the endoscope image is generated. The subject state correction includes items G, H, and I to be corrected.

In the item G, correction information for prompting water sending is generated. Specifically, in the case of an endoscopic scope having a water-sending function, correction information for providing a guide to use the water-sending function to send water is generated.

In the item H, correction information for prompting air sending is generated. Specifically, in the case of an endoscopic scope having an air-sending function, correction information for providing a guide to use the air-sending function to send air is generated.

In the item I, correction information for providing a guide to display a lesion position is generated. Specifically, correction information for providing a guide to change a setting that allows display of the lesion position is generated. For example, display of the lesion position is made possible by, for example, changing the observation mode to the special light mode, enabling lesion detection through image processing, or the like.

In recorded image correction, generated is correction information for correcting the difference between the plurality of reference images captured in advance and the plurality of endoscope images captured and recorded in correspondence with the reference images. The recorded image correction includes items J, K, and L to be corrected.

In the item J, correction information indicating existence of an uncaptured image is generated. Specifically, generated is correction information indicating that the endoscope images to be captured in correspondence with the plurality of reference images include an endoscope image uncaptured.

In the item K, correction information for providing a guide to perform image-capturing according to the predetermined image-capturing order is generated. Specifically, when an image-capturing order is set to the plurality of reference images, correction information for providing a guide to capture the endoscope images corresponding to the reference images according to the set image-capturing order is generated.

In the item L, correction information for selecting the endoscope image is generated. Specifically, generated is correction information that gives an instruction to automatically record the endoscope image having a smaller difference from the reference image among a series of endoscope images captured as a movie or the like. Alternatively, a series of endoscope images captured as a movie or the like is recorded, and correction information is generated, the correction information giving an instruction to automatically delete, among the recorded endoscope images, images other than the endoscope image having a smaller difference from the reference image.

FIG. 9 is an example of a combination of the items described referring to FIG. 6 to FIG. 8. Note that the combination of the items is not limited to the example shown in FIG. 9. The items described referring to FIG. 6 to FIG. 8 may be arbitrarily combined within an allowable combination range.

No. 1 is a combination of the items α(i), c, and A. More specifically, when the appropriate image analysis section 211 determines that the endoscope image is dark, the correction restriction information acquisition section 212 analyzes permissibility of changing the light quantity of the light source or the restriction due to the light quantity settable range. The correction information generation section 213 generates correction information for providing a guide of brightness adjustment feasible under the restriction. This eliminates a guide of light quantity beyond the settable range, and a guide comprehensible for doctors can be provided.

No. 2 is a combination of the items α(ii), d, and B. More specifically, when the appropriate image analysis section 211 determines that the color of the endoscope is not good, the correction restriction information acquisition section 212 analyzes the restriction due to the color adjustable range of the endoscope system. The correction information generation section 213 generates correction information for providing a guide of color adjustment feasible under the restriction. This eliminates a guide of infeasible color beyond the adjustable range, and a guide comprehensible for doctors can be provided.

No. 3 is a combination of the items α(iii), α(iv), and C. More specifically, when the appropriate image analysis section 211 determines that the endoscope image is out of focus, the correction restriction information acquisition section 212 analyzes the restriction due to the adjustable range of the field of view of the endoscopic scope. The correction information generation section 213 generates correction information for providing a guide of field-of-view adjustment feasible under the restriction. This eliminates a guide of an infeasible field-of-view beyond the adjustable range, and a guide comprehensible for doctors can be provided.

No. 4 is a combination of the item α(iii), at least one selected from the items α(i), α(ii), α(iii) and g, and F. More specifically, when the appropriate image analysis section 211 determines that the endoscope image is out of focus, the correction information generation section 213 analyzes the restriction due to at least one of the diameter of the scope, the bending of the scope, the length of the scope, and the size of the lumen. The correction information generation section 213 generates correction information for providing a guide of scope operation feasible under the restriction. This eliminates a guide of infeasible scope operation, and a guide comprehensible for doctors can be provided. The infeasible scope operation is, for example, operation that makes the scope abut against the interior wall of the lumen, or operation beyond the movable range of the scope.

No. 5 is a combination of the items α(iv), e, and D. More specifically, when the appropriate image analysis section 211 determines that the endoscope image is blurred, the correction restriction information acquisition section 212 analyzes the restriction due to the adjustable range of the frame rate or the shutter speed of the endoscope system. The correction information generation section 213 generates correction information for providing a guide of frame rate adjustment or shutter speed adjustment feasible under the restriction. This eliminates a guide of infeasible frame rate adjustment or shutter speed adjustment beyond the adjustable range, and a guide comprehensible for doctors can be provided.

No. 6 is a combination of the items β, g, and E. More specifically, when the appropriate image analysis section 211 determines that the size of the image-captured portion appearing in the endoscope image is inappropriate, the correction restriction information acquisition section 212 analyzes the restriction due to the size or the shape of the lumen. The correction information generation section 213 generates correction information for providing a guide of scope operation feasible under the restriction. This eliminates a guide of infeasible scope operation that makes the scope abut against the interior wall of the lumen, and a guide comprehensible for doctors can be provided.

No. 7 is a combination of the items γ, g, and F. More specifically, when the appropriate image analysis section 211 determines that the image-capturing angle of the image-captured portion appearing in the endoscope image is inappropriate, the correction restriction information acquisition section 212 analyzes the restriction due to the size or the shape of the lumen. The correction information generation section 213 generates correction information for providing a guide of the scope position and the scope angle feasible under the restriction. This eliminates a guide of infeasible scope operation that makes the scope abut against the interior wall of the lumen, and a guide comprehensible for doctors can be provided.

No. 8 is a combination of the items γ, h, and F. More specifically, when the appropriate image analysis section 211 determines that the image-capturing position is inappropriate, the correction restriction information acquisition section 212 analyzes the restriction due to the submucosa state of the image-captured portion. The correction information generation section 213 generates correction information for providing a guide of scope operation feasible under the restriction. The scope operation feasible under the restriction is an operation for changing, when it is determined that the submucosa of the image-captured portion is rough, the image-capturing position to prevent the scope from touching the rough submucosa. This eliminates a guide of scope operation that makes the scope abut against the rough submucosa, and therefore the scope can be guided to an appropriate image-capturing position while preventing bleeding in the case where the lumen is rough.

No. 9 is a combination of the items δ, g, and F. More specifically, when the appropriate image analysis section 211 determines that the image-capturing position is inappropriate, the correction restriction information acquisition section 212 analyzes the restriction due to the size or the shape of the lumen. The correction information generation section 213 generates correction information for providing a guide of the scope position and the scope angle feasible under the restriction. This eliminates a guide of infeasible scope operation guidance that makes the scope abut against the interior wall of the lumen, and a guide comprehensible for doctors can be provided.

No. 10 is a combination of the items δ, h, and F. More specifically, when the appropriate image analysis section 211 determines that the image-capturing angle is inappropriate, the correction restriction information acquisition section 212 analyzes the restriction due to the submucosa state of the image-captured portion. The correction information generation section 213 generates correction information for providing a guide of scope operation feasible under the restriction. The scope operation feasible under the restriction is an operation for changing, when it is determined that the submucosa of the image-captured portion is rough, the image-capturing angle to prevent the scope from touching the rough submucosa. This eliminates a guide of scope operation that makes the scope abut against the rough submucosa, and therefore the scope can be guided to an appropriate image-capturing angle while preventing bleeding in the case where the lumen is rough.

No. 11 is a combination of the items ε, g, and G. More specifically, when the appropriate image analysis section 211 determines that there is a residue remained in the image-captured portion, the correction restriction information acquisition section 212 analyzes the restriction due to the size or the shape of the lumen. The correction information generation section 213 generates correction information for providing a guide of water sending feasible under the restriction. Specifically, the correction information generation section 213 generates correction information for providing a guide of a water-sending direction that facilitates flowing of the residue in view of the size or the shape of the lumen. As a result, when there is a residue, the water-sending direction is guided in view of the size or the shape of the lumen, and therefore the residue is more certainly flowed.

No. 12 is a combination of the items ζ, i, and H. More specifically, when the appropriate image analysis section 211 determines that inflation of the organ is insufficient, the correction restriction information acquisition section 212 analyzes the restriction due to the condition or appearance of the organ. The correction information generation section 213 generates correction information about air sending on the basis of the analysis result. The correction information is a guide indicating necessity/unnecessity of the air sending. Alternatively, the correction information is a guide indicating that the air sending is necessary, and an amount of the air sending. As a result, a guide of the air-sending in view of the condition or the appearance of the ridges of the organ is provided, and therefore a precise guide of necessity/unnecessity of the air sending and the air-sending amount can be provided. Note that the guide of air-sending in view of the condition of the ridges of the organ is particularly effective in a large intestine endoscopic examination.

No. 13 is a combination of the items η, c, and I. More specifically, when the appropriate image analysis section 211 determines that there is a lesion in the image-captured portion, the correction restriction information acquisition section 212 analyzes the restriction as to whether the light source has a function of emitting special light. The correction information generation section 213 generates correction information for providing a guide of light source operation feasible under the restriction. Specifically, the correction information generation section 213 makes decision on the basis of the analysis result of the restriction as to whether to generate only a display indicating the lesion position as correction information or to generate, as correction information, a display indicating the lesion position together with a guide to prompt switching to the special light mode. As a result, taking into consideration whether image-capturing in the special light mode is possible or not, a guide for switching to an infeasible observation mode is not provided, and the guide becomes comprehensible for doctors.

No. 14 is a combination of the items θ, b, and J. More specifically, when the appropriate image analysis section 211 determines that there is an uncaptured image, the correction restriction information acquisition section 212 analyzes the restriction due to the endoscopic scope. Specifically, the correction restriction information acquisition section 212 performs first determination whether the uncaptured image can be captured by the angle operation of the scope front end. When the correction restriction information acquisition section 212 determines that the uncaptured image cannot be captured even by the angle operation, the correction restriction information acquisition section 212 performs second determination whether twisting or insertion/extraction of the insertion section enables capturing of the uncaptured image. The correction information generation section 213 generates a guide of scope operation for capturing the uncaptured image as correction information under the restriction based on the results of the first determination and the second determination. This makes it possible to provide a guide of the operation method of the endoscopic scope required to capture the uncaptured image, and therefore how to operate the endoscopic scope is comprehensible for doctors.

No. 15 is a combination of the items θ, c, and L. More specifically, when the appropriate image analysis section 211 determines that there is a special light image uncaptured, the correction restriction information acquisition section 212 analyzes the restriction as to whether the light source has a function of emitting special light. The correction information generation section 213 generates correction information for providing a guide of light source operation feasible under the restriction. Specifically, the correction information generation section 213 generates a guide prompting switching to the special light mode as correction information when the light source can emit the special light. When the light source cannot emit the special light, the correction information generation section 213 does not generate the guide prompting switching to the special light mode as correction information. As a result, taking into consideration whether the image-capturing in the special light mode is possible or not, a guide for switching to an infeasible observation mode is not provided, and the guide becomes comprehensible for doctors.

No. 16 is a combination of the items λ, b, and K. More specifically, when the appropriate image analysis section 211 determines that image-capturing according to the predetermined image-capturing order is not performed, the correction restriction information acquisition section 212 analyzes the restriction due to the endoscopic scope. Specifically, the correction restriction information acquisition section 212 performs first determination whether the angle operation of the scope front end enables image-capturing according to the image-capturing order. When the correction restriction information acquisition section 212 determines that the image-capturing according to the image-capturing order is not enabled by the angle operation, the correction restriction information acquisition section 212 performs second determination whether twisting or insertion/extraction of the insertion section enables image-capturing in the image-capturing order. The correction information generation section 213 generates, as correction information, a guide of scope operation for performing image-capturing in the image-capturing order under the restriction based on the results of the first determination and the second determination. This makes it possible to provide a guide of the operation method of the endoscopic scope required to perform image-capturing according to the predetermined image-capturing order, and therefore how to operate the endoscopic scope becomes comprehensible for doctors.

No. 17 is a combination of the items μ, f, and L. More specifically, when the appropriate image analysis section 211 determines that a plurality of similar endoscope images is captured, i.e., a plurality of endoscope images having a small difference therebetween is captured, the correction restriction information acquisition section 212 analyzes the restriction due to the storage section of the endoscope system. The restriction due to the storage section is storage capacity of the storage section or remaining capacity of the storage section, or both of them. The correction information generation section 213 generates a guide about deletion of images as correction information. Specifically, when the storage capacity or the remaining capacity is insufficient, a guide to prompt deletion of images is generated. When the storage capacity or the remaining capacity is sufficient, the guide to prompt deletion of images is not generated. As a result, the number of captured images to be stored can be decreased when the storage capacity or the remaining capacity is small, which hardly causes problems of insufficient remaining capacity of the storage section.

3. Second and Third Configuration Examples

Figure 10:
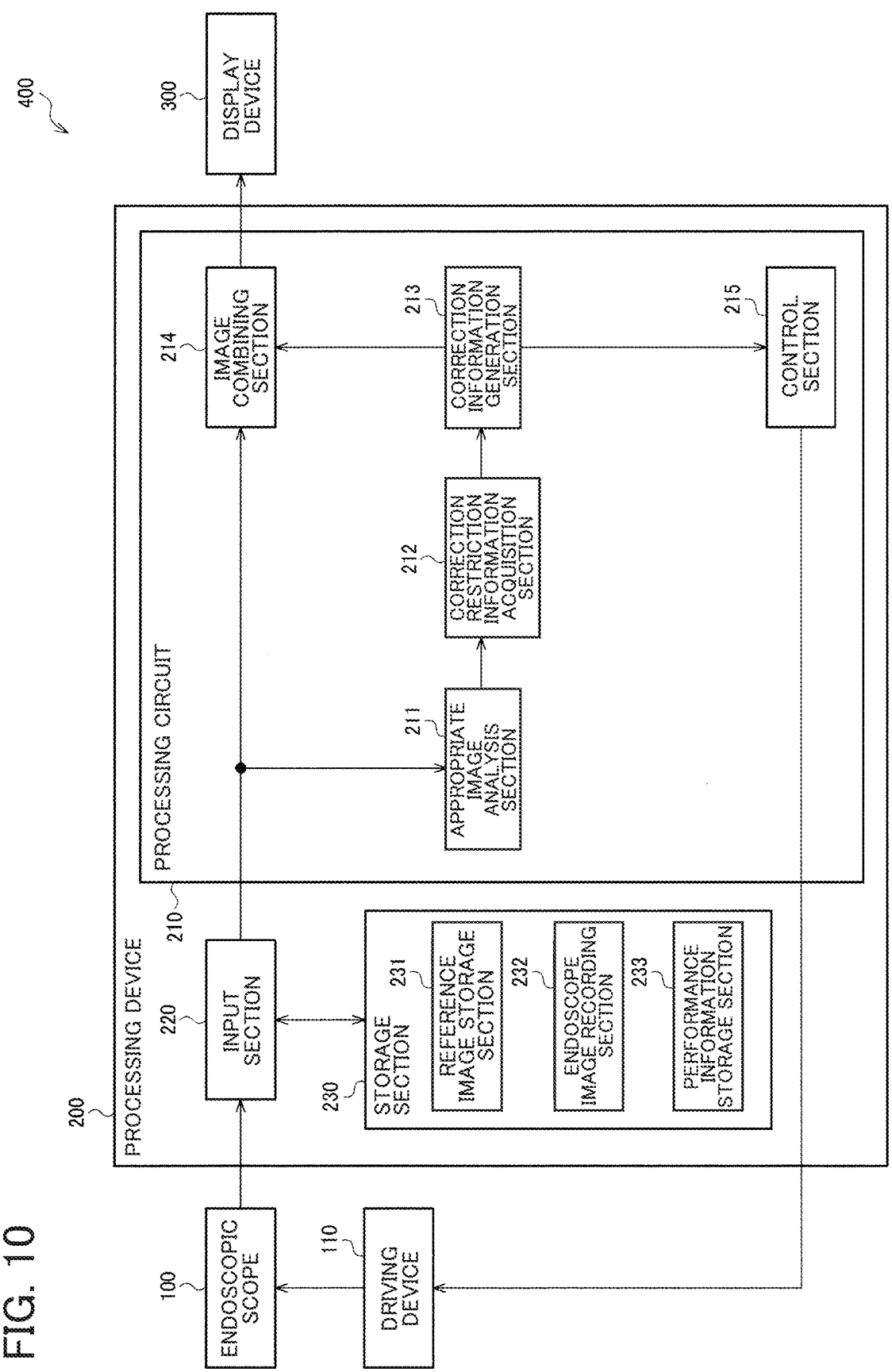
FIG. 10 illustrates a second configuration example of an endoscope apparatus.

FIG. 10 illustrates a second configuration example of the endoscope apparatus 400. The second configuration example is adopted when automatic image-capturing is performed through automatic insertion/extraction of the endoscopic scope. In FIG. 10, the endoscope apparatus 400 further includes a driving device 110. Components same as the components illustrated in FIG. 1 are denoted with the same reference numerals, and description of the components is omitted as appropriate. Note that FIG. 10 omits illustration of the light source 150 and the operation device 350.

The driving device 110 includes an actuator that performs insertion/extraction of the endoscopic scope 100, another actuator that performs angle operation of the front end of the endoscopic scope 100, and a driving circuit that drives these actuators. Furthermore, the driving device 110 may include an actuator that performs water sending, another actuator that performs air sending, and a driving circuit that drives these actuators.

The control section 215 of the processing circuit 210 outputs a control instruction of the automatic insertion/extraction to the driving device 110. On the basis of the control instruction, the driving device 110 automatically inserts/extracts the endoscopic scope 100. The control section 215 of the processing circuit 210 receives an input of correction information from the correction information generation section 213. On the basis of the correction information, the control section 215 outputs a driving instruction for changing the image-capturing conditions to the driving device 110. The driving device 110 performs an actuator control corresponding to the driving instruction to thereby operate the endoscopic scope 100 so as to change the image-capturing conditions. Furthermore, the control section 215 may control the light source 150 on the basis of the correction information to thereby change the image-capturing conditions. Furthermore, the control section 215 may control an image-capturing section of the endoscopic scope 100 on the basis of the correction information. Specifically, the control section 215 may control the frame rate, the shutter speed, the zoom magnification, or the like on the basis of the correction information.

Figure 11:
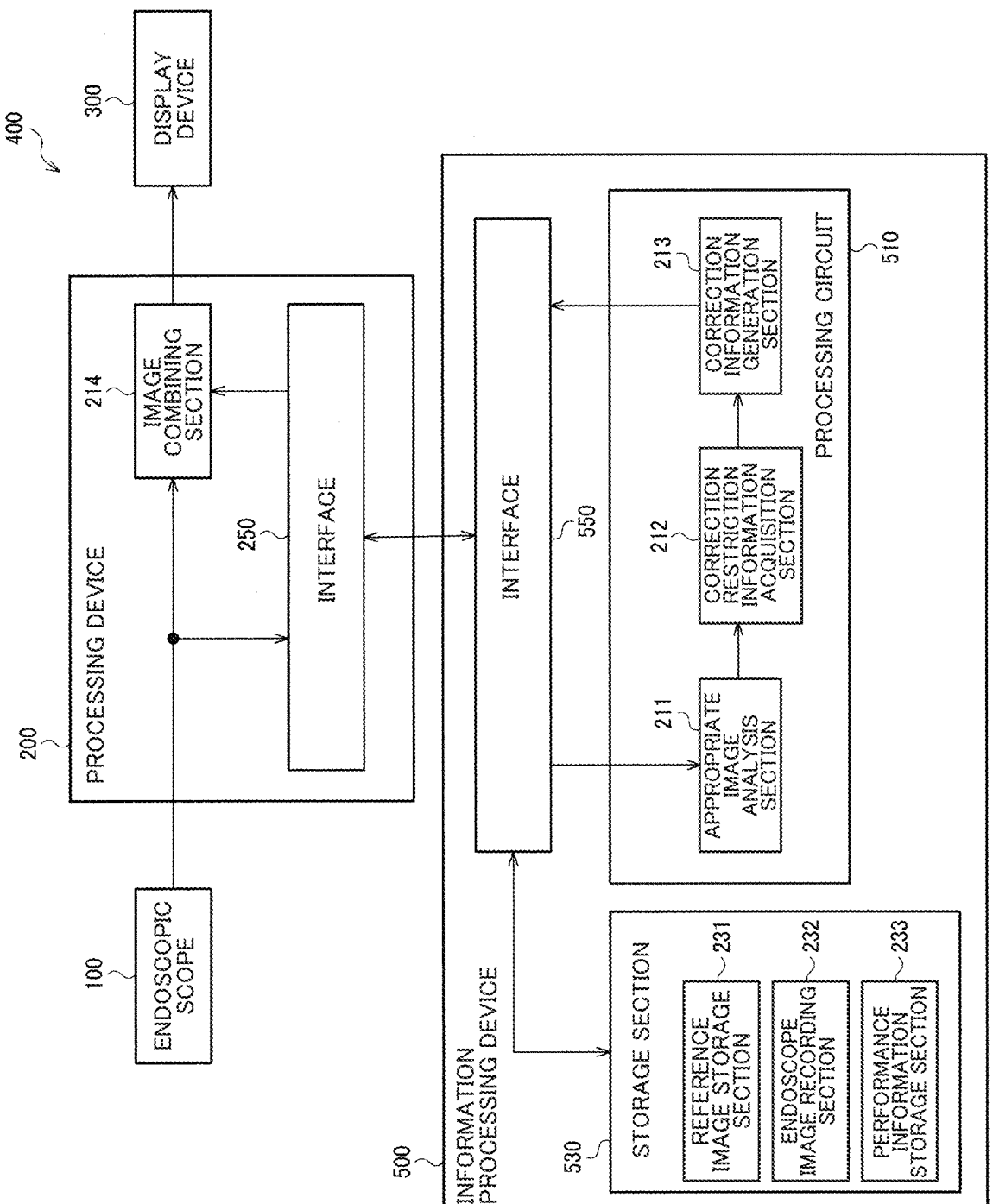
FIG. 11 illustrates a third configuration example of an endoscope apparatus.

FIG. 11 illustrates a third configuration example of the endoscope apparatus 400. In the third configuration example, the endoscope apparatus 400 includes an information processing device 500. Components same as the components illustrated in FIG. 1 are denoted with the same reference numerals, and description of the components is omitted as appropriate. Note that FIG. 11 omits illustration of the light source 150, the operation device 350, and the control section 215.

The processing device 200 includes the image combining section 214 and an interface 250. The information processing device 500 includes an interface 550, a storage section 530, and a processing circuit 510. The information processing device 500 is a personal computer (PC), a server, or the like separately provided in addition to the processing device 200. The information processing device 500 may be configured by a single processing device or a plurality of processing devices. For example, the information processing device 500 may be implemented by a cloud system. The interface 250 and the interface 550 may be a bus communication interface such as a USB or a network communication interface such as a LAN or a WAN.

The interface 250 of the processing device 200 transmits the endoscope image captured by the endoscopic scope 100 to the interface 550 of the information processing device 500. The interface 550 inputs the received endoscope image to the processing circuit 510. That is to say, the interface 550 corresponds to the input section. The processing circuit 210 includes the appropriate image analysis section 211, the correction restriction information acquisition section 212, and the correction restriction information generation section 213, and generates correction information based on the endoscope image to output to the interface 550. The interface 550 transmits the correction information to the interface 250 of the processing device 200. The interface 250 outputs the received correction information to the image combining section 214. The image combining section 214 combines the correction information with the endoscope image, and outputs the combined endoscope image to the display device 300. Note that the storage section 530 may include the reference image storage section 231, the endoscope image recording section 232, and the performance information storage section 233, and the interface 550 may include an access control circuit of the storage section 530.

In FIG. 1, FIG. 10, and FIG. 11, when some of or all of the appropriate image analysis section 211, the correction restriction information acquisition section 212, the correction information generation section 213, the image combining section 214, and the control section 215 are implemented by a program, the endoscope apparatus may be configured as described below.

That is to say, the endoscope apparatus according to this embodiment includes a memory that stores information, and a processor that operates on the basis of the information stored in the memory. The information is, for example, a program and various types of data. The processor executes part of or all of processing of the appropriate image analysis section 211, the correction restriction information acquisition section 212, the correction information generation section 213, the image combining section 214, and the control section 215 described in this embodiment.

The processor includes hardware, and the hardware may include at least one of a circuit for processing a digital signal and a circuit for processing an analogue signal. For example, the processor may be configured by one or more circuit devices mounted on a circuit board or one or more circuit elements. The example of the one or more circuit devices is an IC or the like. The example of the one or more circuit elements is a resistance, a capacitor, or the like. The processor may be a central processing unit (CPU), for example. However, the processor is not limited to the CPU, and it is possible to adopt various types of processors such as a graphics processing unit (GPU), a digital signal processor (DSP), or the like. Furthermore, the processor may be an integrated circuit device such as an application specific integrated circuit (ASIC), a field programmable gate array (FPGA), or the like. Furthermore, the processor may include an amplifier circuit or a filtering circuit for processing the analogue signal. The memory may be a semiconductor memory such as an SRAM and a DRAM, a register, a magnetic storage device such as a hard disk device, or an optical storage device such as an optical disk device. For example, the memory stores a computer-readable command. When the command is executed by the processor, functions of the sections of the endoscope apparatus are implemented as processing. The command mentioned here may be a command of a command set constituting the program, or may be a command that gives an instruction on the hardware circuit of the processor to operate.

Furthermore, the program may be stored in a non-transitory information storage medium that is a computer-readable medium, for example. The information storage medium can be implemented by, for example, an optical disk, a memory card, an HDD, a semiconductor memory, or the like. An example of the semiconductor memory is a ROM. The processing circuit 210 or the processing circuit 510 performs various types of processing according to the present embodiment on the basis of the programs and data stored in the information storage medium. That is to say, the information storage medium stores programs for part of or all of the appropriate image analysis section 211, the correction restriction information acquisition section 212, the correction information generation section 213, the image combining section 214, and the control section 215 to function as a computer. The computer is an apparatus provided with an input device, a processing section, a storage section, and an output section. The program is a program for making the computer execute processing of each section.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
one or more processors configured to:
conduct an analysis to determine whether an endoscope image has been appropriately captured;
acquire correction restriction information including at least one of a restriction regarding a size of a lumen of an image-captured portion or a restriction regarding a submucosa state of the image-captured portion;
generate correction information regarding correction of image-capturing conditions for allowing the endoscope image to be appropriately captured under a restriction of the correction restriction information in a case where it is analyzed that the endoscope image has not been appropriately captured and output the correction information on a monitor; and
when it is determined that the submucosa state is rough, generate and output, as the correction information, information for guiding an endoscope operation for allowing an endoscope to be in an image-capturing position or an image-capturing angle that does not contact the rough submucosa.

2. The endoscope apparatus as defined in claim 1, wherein the one or more processors are configured to:
conduct the analysis by determining whether the endoscope image satisfies a criterion or not;
acquire the correction restriction information about a correction method for correcting the image-capturing conditions such that the endoscope image determined to not satisfy the criterion satisfies the criterion; and
in a case where the correction restriction information indicates no-restriction, generate the correction information which gives an instruction on the correction method, and in a case where the correction restriction information indicates a restriction, generate the correction information based on the correction restriction information.

3. The endoscope apparatus as defined in claim 1, further comprising:
a light source configured to illuminate a field of view of the endoscope image,
wherein the one or more processors are configured to:
conduct the analysis whether the endoscope image has been captured under appropriate brightness or not;
as the correction restriction information, information about a settable range of a quantity of light of the light source based on a type of the light source; and
in a case where determination is made in the analysis that the endoscope image has been captured under inappropriate brightness, generate correction information regarding setting of the quantity of light of the light source on the basis of the information about the settable range of the quantity of light.

4. The endoscope apparatus as defined in claim 1, wherein:
the correction restriction information includes restriction information regarding performance of an endoscopic scope; and
the performance of the endoscopic scope includes at least one of a diameter of an insertion section, an angle of a front end of the insertion section, a length of the insertion section, and an image-capturing field of view.

5. The endoscope apparatus as defined in claim 4, wherein the one or more processors are configured to:
perform first determination whether operating the angle enables the endoscope image to be appropriately captured or not based on a current state and the performance of the endoscopic scope;
perform, in a case where determination is made that operating the angle does not enable the endoscope image to be appropriately captured, second determination whether the endoscope image is appropriately captured by twisting or inserting/extracting the insertion section or not; and
output the correction restriction information based on results of the first determination and the second determination.

6. The endoscope apparatus as defined in claim 1, wherein:
the correction restriction information includes restriction information regarding performance of a light source that illuminates a field of view of the endoscope image; and
the performance of the light source includes at least one of a type of illumination light emittable from the light source, and a settable range of a quality of light.

7. The endoscope apparatus as defined in claim 1, wherein the restriction regarding the size of the lumen is determined from a size, an interval, a depth of ridges in the lumen, or whether a ridge inside exists in the endoscope image or not.

8. The endoscope apparatus as defined in claim 1, wherein the restriction regarding the submucosa state is determined from a color of a submucosa or structure of the submucosa.

9. The endoscope apparatus as defined in claim 1, wherein the one or more processors are configured to:
perform the analysis whether the endoscope image has appropriate quality or not; and
generate, in a case where the endoscope image is determined to not have the appropriate quality, the correction information for correcting the image-capturing conditions such that the endoscope image becomes the appropriate quality.

10. The endoscope apparatus as defined in claim 9, wherein:
the quality of the endoscope image is quality regarding at least one of brightness, a color, a focus, and blurring of the endoscope image, and
the one or more processors are configured to generate, in a case where it is analyzed that the quality of the endoscope image does not satisfy a criterion, the correction information for correcting the quality of the endoscope image.

11. The endoscope apparatus as defined in claim 1, wherein the one or more processors are configured to:
conduct the analysis on a difference between the endoscope image and a reference image; and
generate the correction information for correcting the image-capturing conditions so as to make the difference smaller.

12. The endoscope apparatus as defined in claim 11, wherein the one or more processors are configured to:
analyze a distance between an endoscopic scope and the image-captured portion by comparing a size of the image-captured portion appearing in the endoscope image with a size of the image-captured portion appearing in the reference image; and
generate the correction information for correcting the distance to an appropriate distance.

13. The endoscope apparatus as defined in claim 11, wherein the one or more processors are configured to:
compare an image-capturing angle of the image-captured portion in the endoscope image with an image-capturing angle of the image-captured portion in the reference image; and
generate the correction information for correcting an image-capturing angle of an endoscopic scope to an appropriate angle.

14. The endoscope apparatus as defined in claim 11, wherein the one or more processors are configured to:
compare a position of the image-captured portion in the endoscope image with a position of the image-captured portion in the reference image; and
generate the correction information for correcting an image-capturing position of an endoscopic scope to an appropriate position.

15. The endoscope apparatus as defined in claim 11, wherein the one or more processors are configured to generate, as the correction information, an instruction to make an endoscopic scope reapproach the image-captured portion.

16. The endoscope apparatus as defined in claim 1, wherein the one or more processors are configured to:
analyze a state of the image-captured portion appearing in the endoscope image; and
generate the correction information based on the state analyzed.

17. The endoscope apparatus as defined in claim 16, wherein the one or more processors are configured to:
determine whether a residue exists in the image-captured portion; and
generate, in a case where determination is made that the residue exists in the image-captured portion, the correction information for prompting water sending.

18. The endoscope apparatus as defined in claim 16, wherein the one or more processors are configured to:
determine whether inflation of a lumen in the image-captured portion is appropriate or not; and
generate, in a case where determination is made that the inflation is not appropriate, the correction information for prompting air sending.

19. The endoscope apparatus as defined in claim 16, wherein the one or more processors are configured to:
determine whether a lesion exists in the endoscope image; and
generate, in a case where determination is made that a lesion exists in the endoscope image, the correction information for displaying the lesion.

20. The endoscope apparatus as defined in claim 1, wherein the one or more processors are configured to:
access a memory that stores a plurality of reference images captured in advance;
conducts the analysis on a difference between the plurality of reference images and the endoscope image; and
generate the correction information based on the difference between the plurality of reference images and the endoscope image.

21. The endoscope apparatus as defined in claim 20, wherein the one or more processors are configured to:
determine whether the endoscope image corresponding to each of the plurality of reference images has been captured or not; and
generate, in a case where there is a reference image whose corresponding endoscope image has not been captured, the correction information that notifies that there is an uncaptured image.

22. The endoscope apparatus as defined in claim 20, wherein:
the memory stores an image-capturing order defined in advance to the plurality of reference images; and
the one or more processors are configured to:
determine whether the endoscope image has been captured according to the image-capturing order; and
generate, in a case where determination is made that the endoscope image has not been captured according to the image-capturing order, the correction information that gives an instruction to perform image-capturing according to the image-capturing order.

23. The endoscope apparatus as defined in claim 20, wherein the one or more processors are configured to:
decide, on the basis of the difference, an endoscope image to be recorded in the memory among a plurality of endoscope images captured in time series; or
the memory records the plurality of endoscope images captured in the time series and the processor decides, on the basis of the difference, an endoscope image to be deleted from the memory among the plurality of endoscope images.

24. An information processing method comprising:
conducting an analysis to determine whether the endoscope image has been appropriately captured;
acquiring correction restriction information including at least one of a restriction regarding a size of a lumen of an image-captured portion or a restriction regarding a submucosa state of the image-captured portion;
generating correction information regarding correction of photographing conditions for allowing the endoscope image to be appropriately captured under a restriction of the correction restriction information in a case where it is analyzed that the endoscope image has not been appropriately captured and output the correction information on a monitor; and
when it is determined that the submucosa state is rough, generating and outputting, as the correction information, information for guiding an endoscope operation for allowing an endoscope to be in an image-capturing position or an image-capturing angle that does not contact the rough submucosa.

25. A non-transitory computer-readable storage medium that stores a computer-readable program for causing one or more processors to execute:

conducting an analysis to determine whether the endoscope image has been appropriately captured;

acquiring correction restriction information including at least one of a restriction regarding a size of a lumen of an image-captured portion or a restriction regarding a submucosa state of the image-captured portion;

generating correction information regarding correction of image-capturing conditions for allowing the endoscope image to be appropriately captured under a restriction of the correction restriction information in a case where it is analyzed that the endoscope image has not been appropriately captured and outputting the correction information on a monitor; AND when it is determined that the submucosa state is rough, generating and outputting, as the correction information, information for guiding an endoscope operation for allowing an endoscope to be in an image-capturing position or an image-capturing angle that does not contact the rough submucosa.

* * * * *